United States Patent [19]
Morrison

[11] 3,991,310
[45] Nov. 9, 1976

[54] BIPLANE RADIOGRAPHIC LOCALIZATION OF TARGET CENTER FOR RADIOTHERAPY

[76] Inventor: Richard A. Morrison, 9021 Delmar, Shawnee Mission, Kans. 66207

[22] Filed: Feb. 9, 1972

[21] Appl. No.: 224,712

Related U.S. Application Data

[63] Continuation-in-part of Ser. No. 60,430, Aug. 3, 1970, abandoned, which is a continuation-in-part of Ser. No. 733,585, May 31, 1968, abandoned.

[52] U.S. Cl. ................................ 250/312; 250/313
[51] Int. Cl. ............................................. G03B 41/16
[58] Field of Search ............... 250/65 R, 59, 52, 53, 250/61.5, 60

[56] References Cited
UNITED STATES PATENTS

| | | | |
|---|---|---|---|
| 2,650,308 | 8/1953 | Catlin | 250/509 |
| 2,770,719 | 11/1956 | Simjian | 250/65 R |
| 3,082,322 | 3/1963 | Koerner | 250/61.5 |
| 3,673,394 | 6/1972 | Hartmann | 250/65 R |

Primary Examiner—James W. Lawrence
Assistant Examiner—C. E. Church

[57] ABSTRACT

The center of tissue within a patient to be subjected to radiation treatment is located in terms of coordinates with respect to a predetermined origin defined by three mutually orthogonal reference axes. Projections of at least one of the axes are superimposed upon two radiographs in different radiographic planes showing the tissue center and surrounding features in enlarged dimensions. In order to determine the reduced, true coordinates of the tissue center in cases where frontal and lateral radiographs are obtained, one method is disclosed in which analytic geometry is applied to reduce the values of the projected coordinates. Reduction factors for the two radiographs are also ascertained so that the actual length, width and breadth of the treatment volume may be calculated. Alternatively, a localizer may be employed which positions the radiographs, or slides made therefrom, in orthogonal planes and illuminates the radiographs or slides with point light sources arranged to duplicate the geometry of the X-ray unit utilized in obtaining the radiographs. A transparency having graduated axes thereon is interposed between the light sources and the radiographs or slides and positioned such that projections of the origin of the graduated axes are aligned with the tissue centers on both of the radiographs, permitting the true coordinates and the dimensions of the treatment volume to be directly read from the graduations on the projected axes. A third technique is disclosed in which the true coordinates are determined irrespective of the angular locations of the X-ray focuses, and employs a two-dimensional simulation of the radiographic geometry upon which transverse coordinates from the radiographs are plotted using assumed focus-to-center distances and then translated graphically to find the true coordinates.

3 Claims, 24 Drawing Figures

BIPLANE RADIOGRAPHIC LOCALIZATION OF TARGET CENTER FOR RADIOTHERAPY

CROSS REFERENCE

This application is a continuation in part of my copending application, Ser. no. 60,430, filed Aug. 3, 1970, such earlier application being a continuation in part of application Ser. No. 733,585, filed May 31, 1968 both now abandoned.

Accurate localization of deep seated tumors is essential when radiation treatment is undertaken with curative intent. The treatment is commonly effected with a rotation radiotherapy machine that directs a rotating or stationary beam through the tumor or other tissue to be treated. Such machines, for example, may be of the cobalt, betatron, or linear accelerator type.

In a machine of the mentioned type, the patient normally lies on a treatment stretcher disposed adjacent the axis about which the beam source rotates during operation of the machine. The stretcher is shiftable vertically and horizontally (both laterally and longitudinally of the patient) so that the tumor center may be located on the axis of rotation of the source head and longitudinally of such axis such that the center of rotation of the central ray of the beam is disposed at the tumor center. This, at least, is the ideal alignment of patient and machine assuming that the tumor center is known with absolute precision.

From the foregoing, it may be appreciated that knowledge of the tumor center with respect to a suitable reference is of paramount importance if the radiotherapy is to be effective and the radiation is to be concentrated where needed. Heretofore, a biplane radiographic technique has been employed to localize the tumor center. Frontal and lateral X-ray radiographs of the patient are taken employing a frontal X-ray tube focus directly overhead and a lateral focus displaced 90° therefrom, and any of various approaches are then employed to establish the location of the tumor center in a manner such that the patient may be subsequently aligned with the beam of the rotation radiotherapy machine, including the use of an object, such as a coin, resting on the patient and placed by trial and error until the shadow of the object is in desired alignment with the tumor center images on the radiographs, whereupon the patient is marked to designate the tumor center. Since the projected images of the patient's features in the radiographs are larger than actual size, the object, being of known dimensions, is measured to determine the appropriate reduction factors for the radiographs so that the size of the treatment volume may be calculated.

It is, therefore, an important object of this invention to provide improved methods of localizing a tissue center which are capable of theoretically precise accuracy and which do not employ trial and error techniques or subjective analysis.

As a corollary to the foregoing object, it is an important aim of the present invention to provide improved methods of determining the dimensions of the treatment volume from biplane radiographs and preparing a patient for treatment by the beam of a rotation radiotherapy machine.

Another important object of the present invention is to provide a preferred localization method which also enables the X-ray focuses to be at any desired angular locations without affecting the accuracy of the localization or the dimensional determinations.

Still another important object of the invention is to provide localization apparatus for use in implementing the aforesaid preferred method, wherein the radiographic geometry is simulated in two dimensions and graphical analysis is employed in the localization and the dimensional determinations.

Furthermore, it is specific and important object of the invention to provide an improved method of determining the location of the tissue center in terms of coordinates with respect to a predetermined origin defined by three mutually orthogonal reference axes, wherein analytic geometry is employed to derive the coordinates of the tissue center from projected coordinates thereof determined from anterior-posterior and lateral radiographs.

Additionally, it is another specific and important object of this invention to provide a method of determining the location of the tissue center in terms of coordinates as aforesaid, wherein such coordinates are directly read from anterior-posterior and lateral radiographs or from representations thereof made therefrom, through the use of localization apparatus which duplicates the X-ray geometry and projects graduated axes onto the radiographs or representations thereof.

THE ANALYTIC METHOD — FIGS. 1–9

Figures 1, 2:
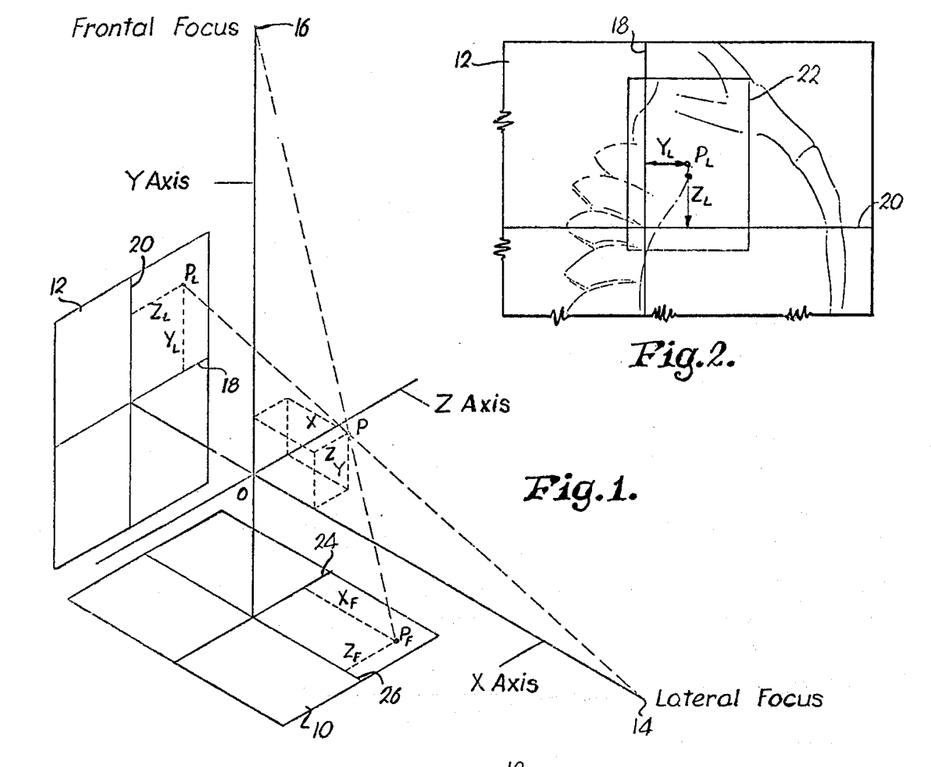
FIG. 1 is a perspective view illustrating the coordinate system and the locations of the X-ray focuses and corresponding radiographs.
FIG. 2 is a fragmentary view of the lateral radiograph.

Referring initially to FIG. 1, mutually orthogonal X, Y and Z reference axes are illustrated which are employed in conjunction with a conventional biplane diagnostic X-ray unit (not shown). The patient is recumbent and lies generally along the Z-axis, and in such position is disposed in overlying relationship to a frontal radiograph 10. The patient thus lies alongside a lateral radiograph 12, the frontal radiograph 10 being disposed in a plane parallel to the XZ-plane, while the lateral radiograph 12 is disposed in a plane parallel to the YZ-plane. The point P represents the center of the tissue within the patient to be treated; such center will be referred to in the remainder of this specification as the target center or tumor center. The coordinates of the point P are its distances from the respective coordinate planes measured parallel to the coordinate axes. The X-coordinate is the distance from the YZ-plane, a sagittal plane in the patient, measured parallel to the X-axis, i.e., from side to side in the patient. The Y-coordinate is the distance from the XZ-plane, a frontal plane in the patient, measured parallel to the Y-axis, i.e., from back to front in the patient. The Z-coordinate is the distance from the XY-plane, a transverse plane in the patient, measured parallel to the Z-axis, i.e., from foot to head.

$X_F$ and $Z_F$ are the projections of the X and Z coordinates of the target center on the frontal radiograph 10. $Y_L$ and $Z_L$ are projections of the Y and Z coordinates on the lateral radiograph 12. The positive side of the X and Y axes is on the same side as the lateral and frontal (overhead) X-ray focuses 14 and 16 respectively. The positive side of the Z-axis is toward the head of the patient.

If $S_L$ and $S_F$ are the focus-to-origin distance for the lateral and frontal projections respectively, and $F_L$ and $F_F$ are the corresponding focus-to-film distances, then $$\frac{X}{X_F} = \frac{S_F - Y}{F_F} \tag{1}$$

$$\frac{Y}{Y_L} = \frac{S_L - X}{F_L} \tag{2}$$

It will be noted that when the focus-to-film distances, $F_F$ and $F_L$, and the focus-to-origin distances, $S_F$ and $S_L$, are constants, equations (1) and (2) may be solved for X and Y when $X_F$ and $Y_L$ are also known.

Continuing, if $R_F$ is the reduction factor for the target center on the frontal radiograph 10 and $R_L$ is the reduction factor for the target center on the lateral radiograph 12, i.e.

$$R_F = \frac{X}{X_F} = \frac{Z}{Z_F} \tag{3}$$

$$R_L = \frac{Y}{Y_L} = \frac{Z}{Z_L} \tag{4}$$

then from equations (1) and (2)

$$R_F = \frac{S_F - Y}{F_F} \tag{5}$$

$$R_L = \frac{S_L - X}{F_L} \tag{6}$$

Thus, the reduction factor for the target center on the lateral radiograph 12 depends only on the X-coordinate, and the reduction factor for the target center on the frontal radiograph 10 is determined only by the Y-coordinate when $F_L$, $F_F$, $S_L$ and $S_F$ are known constants.

The lateral radiograph 12 is shown in FIG. 2 disposed with the projection 18 of the Z-axis vertically oriented and the projection 20 of the Y-axis horizontally oriented, positive values of Z and Y being up and to the right from the projected origin, respectively. The radiograph 12 shows the upper chest region of the patient as viewed laterally. A field of treatment is defined by the rectangle 22, the projected target center $P_L$ being at the center thereof.

Figure 3:
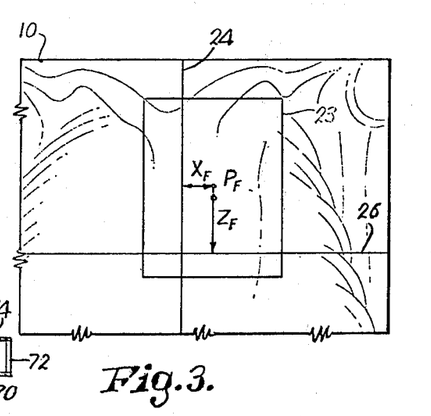
FIG. 3 is a fragmentary view of the frontal radiograph.

Similarly, in FIG. 3 the frontal radiograph 10 shows the upper chest region of the patient as viewed from above with the patient reclining on his back, the projected Z and X axes being illustrated at 24 and 26 respectively. The field of treatment is defined by the rectangle 23, the center thereof being the frontal projection of the target center $P_F$.

Figure 4:
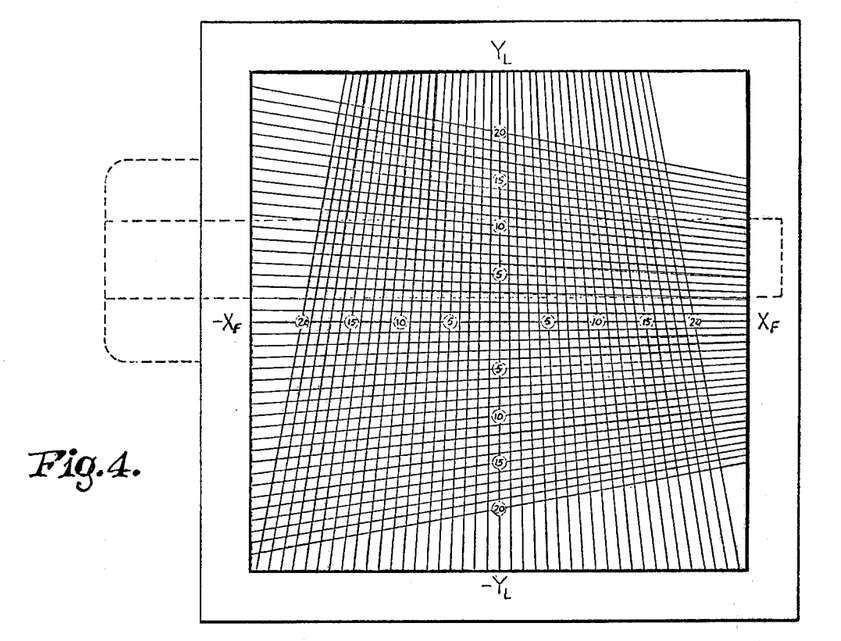
FIG. 4 is an illustration of a graph utilized to facilitate the reduction of projected coordinates to true coordinates and the calculation of reduction factors.
Figure 5:
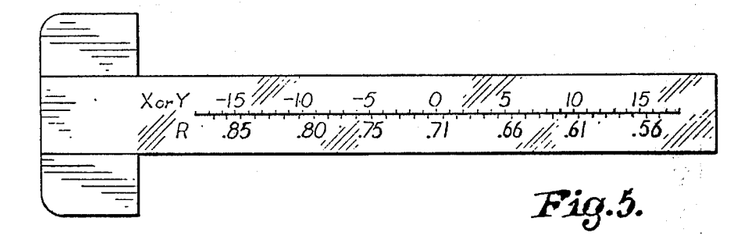
FIG. 5 is an illustration of a T square for use in conjunction with the graph of FIG. 4.

As will be discussed fully hereinafter, the graph and T square in FIGS. 4 and 5 are employed to facilitate the reduction of the projected coordinates $X_F$, $Y_L$, and $Z_F$ or $Z_L$ of the target center to the true coordinates X, Y and Z thereof. Additionally, the graph and T square permit direct reading of reduction factors utilized to compute the actual length, width and breadth of the treatment volume. The straight lines in the graph of FIG. 4 extending in the same general direction as the X-axis but diverging in the $-X_F$ direction represent the diverging rays of X-ray radiation traveling from the lateral focus 14 to the lateral radiograph 12. Similarly, the straight lines in the graph extending in the general direction of the Y-axis and diverging in the $-Y_L$ direction represent the rays of the X-ray radiation traveling from the frontal focus 16 to the frontal radiograph 12. It should be understood that the focus is the point within the X-ray tube from which the radiation emanates. The intersecting straight lines in the graph define the various values of $X_F$ and $Y_L$ in equations (1) and (2) above, the T square being transparent and scaled for direct reading of either the true X or y coordinate and the reduction factor $R_L$ or $R_F$. It is assumed that the X-ray unit to be utilized has the same focus-to-origin and focus-to-film distances frontally and laterally, thus both $R_F$ and $R_L$ may be read from the same scale R.

A localizer frame 28 for use with the X-ray unit is shown in FIGS. 6–9. The frame 28 is rectangular in configuration and includes a pair of spaced, upstanding sides 30 and 32 and top and bottom members 34 and 36 respectively. The bottom member 36 overlies the table 38 of the X-ray unit, the frame 28 being held in place on table 38 by L-shaped brackets 40 depending from side 32 which cooperate with a manually rotatable eccentric 42 operated by a handle 44. The eccentric 42 is mounted on the underside of the bottom member 36 adjacent the side 30, the eccentric 42 and brackets 40 thus forming a clamp which may be brought to bear against the longitudinal edges of table 38 by operation of the handle 44 to effect inward displacement of the surface of the eccentric 42.

A platform 46 is separate from frame 28 and extends therethrough in parallelism with table 38 for the purpose of supporting the patient thereon in a reclining position. The elevation of the platform 46 with respect to table 38 is controlled by blocks 48 under each end of the platform 46.

A cassette holder 50 is secured to the upper surface of the bottom frame member 36, and a second cassette holder 52 is secured to the inner surface of the side 32 of frame 28. The holders 50 and 52 are for the cassettes containing initially unexposed film that will ultimately become the frontal and lateral radiographs 10 and 12 discussed above and depicted in FIGS. 1–3.

Figure 6:
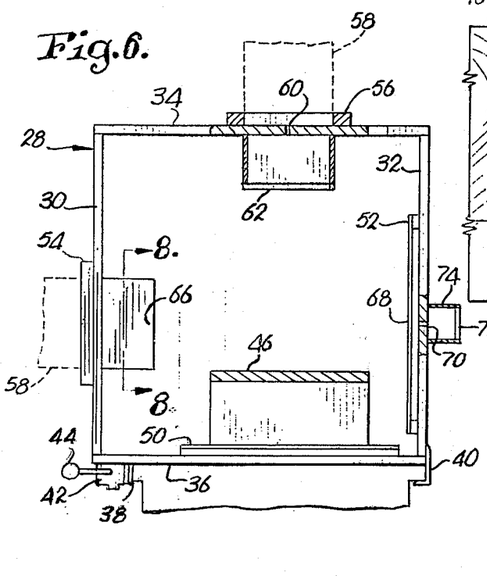
FIG. 6 is an end view of a localizer frame shown secured to the table of a biplane diagnostic X-ray unit.
Figure 7:
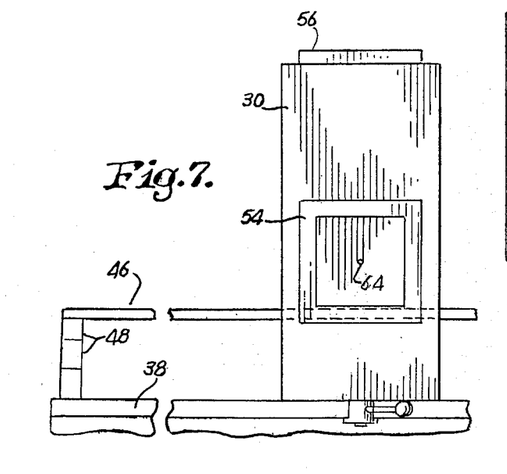
FIG. 7 is a side view of the frame shown in FIG. 6.
Figures 8, 9:
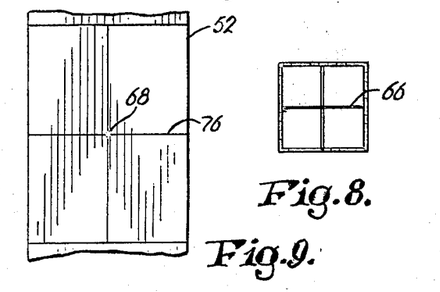
FIG. 8 is a cross-sectional view taken along line 8—8 of FIG. 6.
FIG. 9 is a fragmentary, elevational view showing the cassette holder of the frame for the lateral radiograph.

The side 30 and the top member 34 of the frame 28 are provided with rectangular receptacles 54 and 56 respectively, each of the latter being dimensioned to receive the X-ray tube collimator 58 illustrated in FIG. 6 in phantom lines. An optical sight for the Y-axis is formed by an aperture 60 in the top member 34 which is centered with respect to the collimator receptacle 56. Cross hairs 62 are supported within the frame 28 in spaced relationship to the aperture 69 to complete the sight. Similarly, an aperture 64 through side 30 is centrally disposed within receptable 54 and cross hairs 66 (shown in detail in FIG. 8) are supported in inwardly spaced relationship to the aperture 64.

The lateral aperture 64 and associated cross hairs 66 are aligned with an opening 68 in the lateral cassette holder 52, such opening 68 being in turn aligned with a second opening 70 in side 32 and a sighting aperture 72 formed in the closed end of a tube 74 extending laterally outwardly from side 32. A grid 76 is formed by a pair of cross wires and is embedded in the front of the cassette holder 52 with the crossing point thereof centered on opening 68, as is clear in FIG. 9. The cross wires forming grid 76 are orthogonal to each other and cast a shadow on the lateral radiograph 12 in order to superimpose a projection of the Y and Z axes thereon. Similarly, a second grid (not shown) is embedded in the upper surface of the cassette holder 50 to cast a shadow of the X and Z axes on the frontal radiograph 10.

It should be understood that the sighting aperture 72 and the grid 76 of the lateral cassette holder 52 also form a sight which is aligned with the aperture 64 and the cross hairs 66 on the opposite side of the frame 28 to define the X-axis. The aperture 60, cross hairs 62, and the grid in cassette holder 50 are in mutual alignment orthogonally of the X-axis to define the Y-axis and the origin O at the intersection of such axes. Furthermore, the frame 28 is accurately constructed so that the cassette for the frontal film, upon insertion into holder 50, will lie in a plane parallel to the XZ-plane and the wires of the grid will extend in parallelism to the respective X and Z axes. Manifestly, the cassette holder 52 positions the lateral cassette in a plane parallel to the YZ-plane and the wires of the grid 76 extend in parallelism to respective Y and Z axes.

PROCEDURE — FIGS. 1–9

The patient is placed in the treatment position on the platform 46 within the localizer frame 28. The physician or technician will, or course, be aware of the region within the patient's body containing the tissue to be treated. The localizer frame 28 is moved longitudinally of the table 38 until the origin O (FIG. 1) is near the target center, whereupon the frame 28 is securely clamped to the table 38 by rotating the handle 44.

For three-point localizations, an upper point and two lateral points are marked on the patient or the treatment shell in instances where the patient is fitted with such a shell. This is effected by sighting through the aperture 60 in the top 34 of the frame 28 and marking the point on the patient where the cross hairs 62 are seen to intersect. In similar fashion, the technician or physician views the patient through both of the lateral sights and places a mark on the patient's body or treatment shell at the point where the cross hairs 66 are seen to intersect, and at the point where the wires of the grid 76 are seen to intersect. A wax pencil may be employed for this purpose.

For one-point localizations, frontal sighting is effected as before and an anterior mark is placed on the patient. Lateral sighting is then effected in one direction in order to ascertain the location of the X-axis so that the distance from the X-axis to the upper surface of the platform 46 may be measured. Since the platform 46 is parallel to the XZ-plane, this distance is the same as the origin-to-platform distance.

With the film-containing cassettes loaded in the cassette holders 50 and 52, the frontal and lateral films are exposed to obtain the frontal and lateral radiographs 10 and 12. FIG. 6 illustrates that the X-ray tube collimator 58 in its two positions registers with receptacles 54 and 56 during exposure of the two films, the receptacles 54 and 56 assuring that the center of the path of X-rays coincides with the X and Y axes respectively defined by the localizer sights. It is important, of course, that the patient and the localizer frame 28 remain in their same relative positions between marking and completion of the exposures.

The lateral radiograph 12 is routinely placed on a view box so that the positive side of the Y-axis is to the right and the positive side of the Z-axis is up, as illustrated in FIG. 2. Similarly, the frontal radiograph 10 is placed on an adjacent view box so that the positive side of the X-axis is to the right and the positive side of the Z-axis is up, as illustrated in FIG. 3. Next, the rectangles 22 and 23 are drawn to define the lateral and frontal treatment fields; the centers of the fields $P_L$ and $P_F$ are the projections of the target center P on the lateral and frontal radiographs respectively, and represent the point at which radiation is to be concentrated during subsequent treatment on the rotation therapy machine.

With the projections of the target center marked on the radiographs, the projections of the X, Y and Z coordinates thereof are measured, such coordinate projections being represented by the distances $X_F$, $Y_L$, and $Z_F$ or $Z_L$ in FIGS. 1–3. (It may be appreciated that, insofar as determining the projected Z coordinate is concerned, either the lateral or frontal radiograph may be used since the projection of the Z coordinate is seen on both.) The projection of the width of the treatment volume is determined from the frontal radiograph 10 by measuring the side of the rectangle 23 parallel to the projected X-axis; the breadth of the treatment volume is determined by measuring the side of the rectangle 22 in the lateral radiograph 12 parallel to the projected Y-axis 20; and the length of the treatment volume is determined by measuring the remaining side of either of the two rectangles 22 or 23 as selected by the physician.

Once the projected X and Y coordinates of the target center P are ascertained, equations (1) and (2) above may be solved since $X_F$ and $Y_L$ are now known and $S_F$, $S_L$, $F_F$ and $F_L$ are known from the dimensions of the X-ray unit and the localizer frame 28. To facilitate the solving of these equations and determine the reduction factors $R_F$ and $R_L$ given by equations (5) and (6), the graph and T square of FIGS. 4 and 5 are employed. The position of the tumor center in terms of $X_F$ and $Y_L$ is plotted on the graph and the T square is then applied thereto parallel to the X-axis as illustrated by the phantom lines in FIG. 4. The T square is shifted until the coordinate and reduction factor scales intersect the plotted point. The true value of X is then read from the coordinate scale (designated X or Y on the T square) and the reduction factor $R_L$ is read from the scale designated R on the T square. The T square is then applied to the graph parallel to the Y-axis so that the true coordinate and $R_F$ may be directly read from the T square scales. Once the reduction factors for the two radiographs have been determined, the true Z coordinate of the target center and the actual length, width, and breadth of the treatment volume may be calculated by multiplying the values measured from the radiographs by the appropriate reduction factor.

At the time of treatment, the patient is placed in the treatment position on the stretcher of the rotation therapy machine and the stretcher is oriented such that the origin 0 within the patient is placed at the center of rotation of the source head. This is facilitated by a three-point light localizer fastened to the source head, such localizer being a conventional device utilized to project three points of light onto the patient, one anterior point and two lateral points projected onto the patient from opposite sides along a path orthogonal to the anterior path of projection. The three-point light localizer, therefore, accurately duplicates the paths of the central ray of the beam from the source head which are traversed when the head is directly above the patient or displaced 90° in either direction. In the case of one-point localizations, the overhead light localizer in the source head is centered on the anterior mark and the treatment stretcher is raised to a height such that the axis-to-stretcher distance of the therapy machine equals the origin-to-platform distance previously noted when utilizing the localizer frame 28.

After the patient is positioned with the origin located on the center of rotation of the source head, the stretcher (and patient or treatment shell) is moved laterally through the X distance, vertically through the Y distance, and longitudinally through the Z distance to place the target center at the center of rotation. Utilizing the three-point light localizer on the source head, new marks are made on the patient or shell to designate the target center so that, for subsequent treatments, the center of rotation may be located at the target center without first locating the target center at the origin and then shifting the stretcher through the coordinates. For one-point localizations a new anterior mark is made and the new height of the treatment stretcher is noted. It is now assumed that the central ray of the beam from the source head will intersect the target center irrespective of the angular position of the head, since the center of rotation of the head is accurately located at the target center.

DIRECT READING OF COORDINATES — FIGS. 10–19

Figures 10, 13, 14, 19:
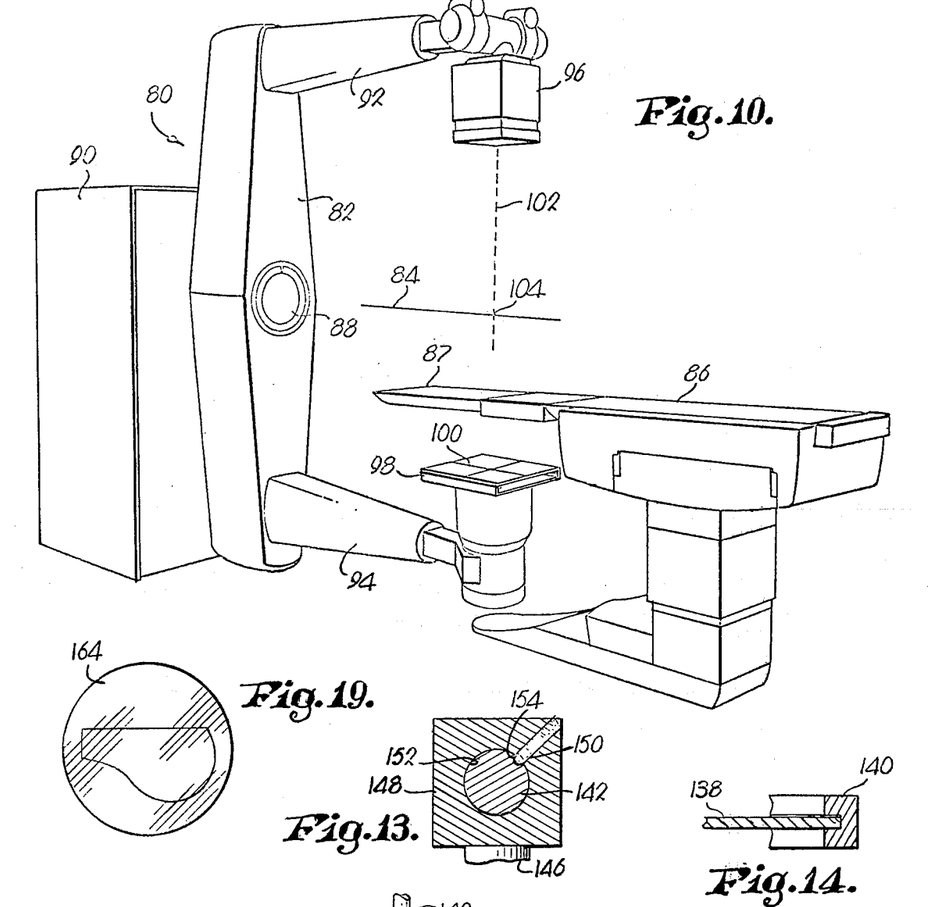
FIG. 10 is a perspective view of a teletherapy simulator.
FIG. 13 is a cross-sectional, detailed view taken along line 13—13 of FIG. 12.
FIG. 14 is a fragmentary, enlarged, cross-sectional view through the slotted rim of the holder for the transparency.
FIG. 19 is an illustration of an exemplary overlay for use in conjunction with a lateral slide corresponding to the frontal slide shown in FIG. 18.

A teletherapy simulator 80 is illustrated in FIG. 10 and has an arm 82 rotatable about a horizontal axis 84 which extends above a couch 86 longitudinally thereof. A rotational scale 88 enables the angular position of the arm 82 relative to the vertical to be read by an operator of the machine. A drive for the arm 82 is located within a housing 90 and is controllable in a manner to permit the arm 82 to be rotated to any angular position about the axis 84.

A pair of booms 92 and 94 extend horizontally from opposite ends of the arm 82, the boom 92 serving to support a diagnostic X-ray source head 96. A cassette holder 98 is mounted on the boom 94 and has a grid 100 thereon in the form of a pair of cross wires embedded in the upper surface thereof. The grid 100 is in a horizontal plane and the center crossing thereof is aligned with a vertical axis 102 which is the central axis of the X-ray beam emanating from the head 96. The simulator 80 is advantageously employed in radiotherapy since such apparatus duplicates the geometry of the rotation radiotherapy machine that will ultimately be utilized to treat the patient. The actual radiotherapy machine, of course, does not employ a cassette holder 98 and a curative radiation source is utilized rather than the X-ray head 96.

Biplane radiographs are obtained in much the same general manner as in the analytic method described hereinabove with respect to FIGS. 1–9. However, the simulator 80 eliminates the need for the localizer frame 28 shown in FIGS. 6–9. Accordingly, taking the radiographs is greatly simplified and thus facilitates the practice of the present invention utilizing either the analytic method set forth hereinabove or the direct reading method to be hereinafter described.

The vertical axis 102 illustrated in FIG. 10 is analogous to the Y axis shown in FIG. 1. In the position illustrated, a frontal radiograph is obtained with the patient positioned on the couch as previously described with reference to the platform 46 within the localizer frame 28. The head of the patient is normally at the left end 87 of the couch 86 on the extension thereof which projects toward the arm 82. Accordingly, the rotational axis 84 corresponds to the Z-axis illustrated in FIG. 1. A lateral radiograph is obtained by rotating the arm 82 counterclockwise through a displacement of 90°. Intersection 104 of the axes 84 and 102 defines the center of rotation of the head 96, thus the new central axis of the X-ray beam for the lateral radiograph passes through the center of rotation 104 and is perpendicular to the plane of the axes 84 and 102. Accordingly, the central axis of the X-ray beam that exposes the lateral radiograph corresponds to the X-axis illustrated in FIG. 1. It may be noted that the lateral focus and lateral radiograph are reversed in this example as compared with the illustration in FIG. 1, but this is a matter of procedural preferences in the practice of the invention and has no effect on the operational principle. Therefore, it will be assumed for purposes of illustration that the radiographs obtained are identical to those illustrated in FIGS. 2 and 3 and discussed hereinabove.

Figure 15:
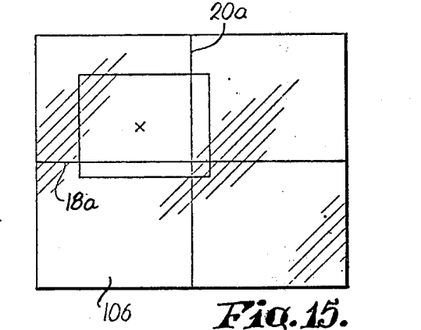
FIG. 15 is a view of a slide prepared from the lateral radiograph of FIG. 2.

The grid 100 causes projections of the Y and Z axes to be superimposed upon the lateral radiograph, and projections of the X and Z axes to be superimposed upon the frontal radiograph. Instead of marking the target center and treatment volume directly on the radiographs, however, transparent slides 106 and 108 (FIGS. 15 and 16) are placed in overlying relationship to the lateral and frontal radiographs respectively. Referring to FIG. 15, it may be seen that the lateral slide 106 has crossed, orthogonal lines 18a and 20a thereon, the slide 106 and the lateral radiograph being oriented with the lines 18 and 18a in register and the lines 20 and 20a in register. The target center and the treatment volume are then marked as before but such markings are placed on the slide 106 rather than directly on the radiograph. Accordingly, the finished slide 106 appears as shown in FIG. 15. This same procedure is followed with respect to the frontal slide 108 which has lines 24a and 26a thereon.

Referring to FIGS. 11-14, a localizer 110 is illustrated that permits the true coordinates of the target center and the dimensions of the treatment volume to be read directly from the lateral and frontal slides 106 and 108. An upright frame 112 is provided with a horizontal platform 114 and a pair of opposed, vertical walls 116 and 118 extending upwardly from the platform 114. A top 120 spans the walls 116 and 118 to provide a closed, square frame open at the front and rear as is clear in FIGS. 11 and 12. A U-shaped guide 122 on the inside of the wall 118 receives the lateral slide 106, and a U-shaped guide 124 on the platform 114 receives the frontal slide 108.

Figure 11:
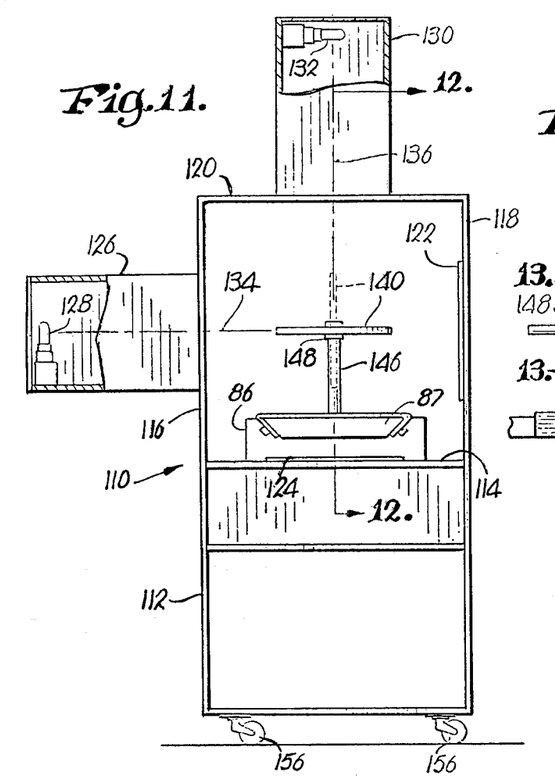
FIG. 11 is a front elevational view of a localizer that duplicates the geometry of the simulator.
Figure 12:
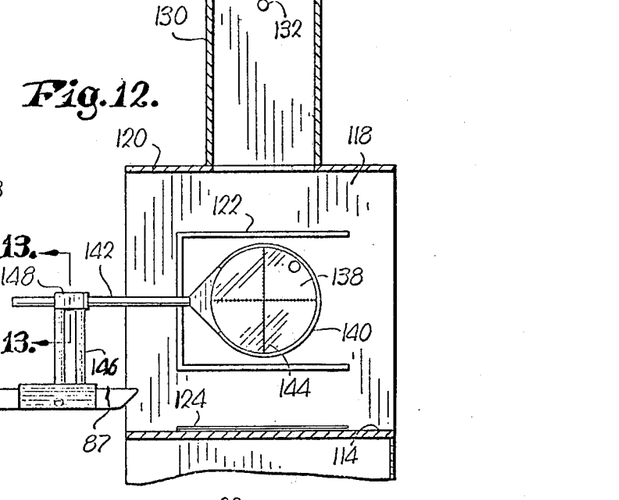
FIG. 12 is a vertical sectional view taken along line 12—12 of FIG. 11.

A housing 126 extends laterally from the wall 116 and has an electric lamp 128 therein which provides an essentially point light source for directing light rays toward the opposite wall 118. Similarly, a housing 130 extends upwardly from the top 120 and has an electric lamp 132 therein which illuminates the platform 114. The paths of the central light rays of the lamps 128 and 132 are illustrated at 134 and 136 respectively.

A transparency 138 in the form of a transparent disc is rotatably held in a slotted rim 140 secured to one end of a horizontal shaft 142. The rim 140 provides a holder for the transparency 138, the latter having orthogonal, graduated axes 144 thereon. A mount 146 for the shaft 142 is advantageously secured to the end 87 of the couch 86 when the latter is not in use with the simulator 80, since couches of this type are provided with internal mechanism for shifting the couch vertically and laterally in three orthogonal directions.

The upper end of the mount 146 comprises a block 148 bored to receive the shaft 142, as is clear in FIG. 13. A detent 150 in the block 148 is receivable within either of two recesses 152 or 154 spaced 90° apart about the axis of the shaft 142. Accordingly, the shaft 142 and hence the transparency 138 are releasably held in either of two operative positions as illustrated in FIG. 11 by the full and broken lines.

In the arrangement illustrated where the couch 86 is utilized as a shiftable support for the transparency 138, the bottom of the localizer 110 may be advantageously provided with casters 156 to facilitate movement of the localizer 110 to a position where the transparency 138 is centered with respect to the viewing plane of the frontal slide 108 within guide 124. It should be noted that the platform 114 and the right wall 118 serve to support the frontal and lateral slides 108 and 106 in orthogonal viewing planes, the slides being held in place by the confines of the guides 122 and 124 into which the slides are inserted.

The initial procedure followed in utilizing the simulator 80 and the localizer 110 is similar to that as discussed above with respect to the analytic localization method. The patient is placed on the couch 86 in the treatment position, and the couch top and patient are then moved longitudinally, vertically and laterally until the target center is near the center of rotation 104, which is the origin of the reference axes. The X-ray head 96 is provided with a light localizer to facilitate the marking of one upper and two lateral points on the patient, or treatment shell, to designate the position of the center of rotation 104. The lateral points, of course, are marked with the head 96 rotated at 90° to either side of the vertical. Alternatively, the patient may be marked in accordance with a one-point localization as discussed hereinabove, rather than the three-point localization.

The frontal and lateral radiographs are then taken and the slides 106 and 108 are appropriately marked to designate the projections of the target center and the treatment volume. The slides are slipped into the guides 122 and 124 of the localizer 110 and the lamp 132 is energized to illuminate the frontal slide 108 which is now disposed substantially in the plane of the upper surface of the platform 114. At this juncture it should be understood that the distances from the sources within the lamps 132 and 128 to the slides 108 and 106 respectively duplicate the corresponding focus-to-film distances in the simulator 80. Since the focus-to-film distance regardless of the angle remains the same in the simulator 80, the source to slide distances in the localizer 110 are equal. Such distances are measured along the paths 134 and 136 of the central rays of the light sources, the paths 134 and 136 being perpendicular to the planes of the slides 106 and 108 respectively. Furthermore, the geometry of the localizer 110 is such that the paths 134 and 136 intersect to define a crossing point analogous to the center of rotation 104 in the simulator 80. Accordingly, the light source to light crossing distance along each of the paths 134 and 136 is equal to the distance from the X-ray focus to the center of rotation 104 in the simulator 80.

Figure 16:
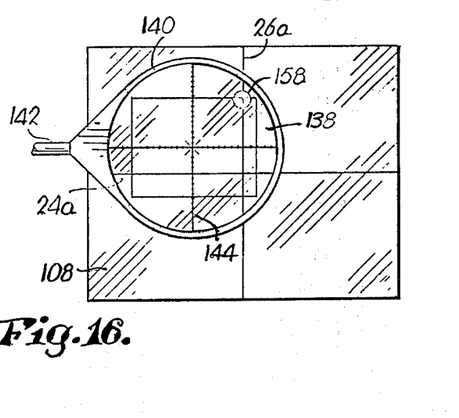
FIG. 16 is a view of a slide prepared from the frontal radiograph of FIG. 3, and illustrates the transparency positioned thereover.
Figure 17:
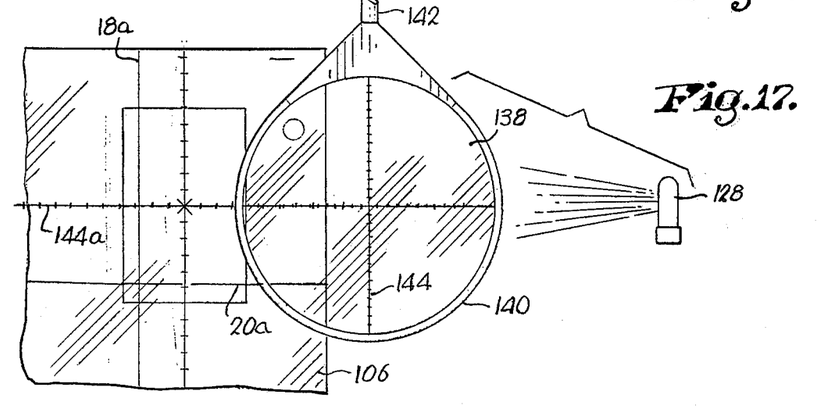
FIG. 17 is an exploded view illustrating the projection of the graduated axes on the transparency onto the lateral slide.

With the transparency 138 in its horizontal position as illustrated in full lines in FIG. 11, it will be appreciated that the transparency 138 is in a plane parallel to the plane of the frontal slide 108. The operator views the shadows cast by the graduated axes 144 on the frontal slide 108 and shifts the couch 86 as necessary to position the projection of the origin of the graduated axes 144 in alignment with the projection of the target center mark on the frontal slide 108. This is depicted in FIG. 16 which is a plan view showing the origin of the graduated axes 144 centered on the target center mark. To facilitate alignment, an opening 158 in the transparency 138 allows insertion of a finger to permit manual rotation of the transparency disc within the rim 140. Besides centering the projection of the origin on the target center mark, it may be noted in FIG. 16 that each of the graduated axes 144 is in parallel alignment with a corresponding axis line on the frontal slide 108.

The operator now energizes the lamp 128 and rotates the transparency 138 to the vertical position thereof shown in broken lines in FIG. 11 and full lines in FIG. 12. In this operative position the transparency 138 is in a plane parallel with the plane of the lateral slide 106. The transparency 138 is shifted vertically upwardly or downwardly as necessary to center the projection of the origin of the graduated axes 144 on the target center mark on the lateral slide 106. Parallel relationship of the projected graduated axes 144 and the axis lines on the slide 106 is maintained. The operator should now return the transparency 138 to the horizontal position and recheck the alignment of the projections on the frontal slide 108. Once assured that proper alignment exists with respect to both of the slides, the true coordinates of the target center are read directly from the projections of the graduated axes 144. For example, referring to FIG. 17, the projections of the graduated axes 144 are illustrated at 144a on the lateral slide 106. Assuming that the graduations on the axes 144 are spaced at one centimeter intervals, it may be seen that the longitudinal or Z coordinate is 4.7 centimeters, the distance as measured by the projected graduations from the target center to the axis line 20a. The anterior-posterior or Y coordinate is 2.7 centimeters, the distance indicated by the projected graduations from the target center to the axis line 18a. In an analogous manner, the lateral or X coordinate is found from viewing the projected graduations on the frontal slide 108. Furthermore, in order to determine the dimensions of the treatment volume, it is evident that the projections of the centimeter scales are read on the lateral and frontal slides within the rectangles defining the volume.

Knowing the true coordinates of the target center, the patient is again placed on the simulator couch 86 and positioned with the center of rotation 104 at the reference origin previously marked when obtaining the radiographs. The patient is then moved laterally, longitudinally and vertically through distances equal to the coordinates to thereby place the center of rotation 104 at the target center. The patient is now remarked using the light localizer within the X-ray head 96 so that the patient may subsequently be placed on the rotation radiotherapy machine and properly positioned without the necessity of shifting the patient through the coordinates.

Figure 18:
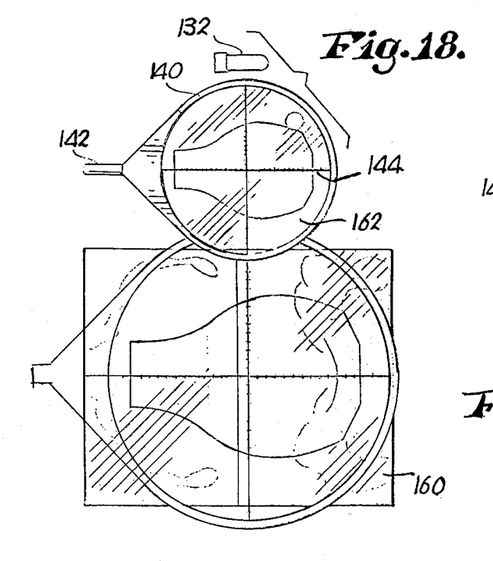
FIG. 18 is an exploded view illustrating the projection of the graduated axes onto another exemplary frontal slide, wherein an overlay is used in conjunction with the transparency.

An alternative procedure is illustrated in FIG. 18. A frontal slide 160 is shown having the anatomy required to localize the target volume drawn thereon. In the present example the pelvic region of a patient is depicted. Rather than initially marking the projection of the target center and the bounds of the treatment volume on the slide 160, an overlay 162 is prepared having an actual size frontal outline thereon of the target volume. The overlay 162 is placed on the transparency 138 with the outline centered with respect to the origin of the graduated axes 144. Alignment utilizing the localizer 110 is then effected as before, except that the shadow of the frontal outline is now properly positioned to fit the features of the anatomy shown on the slide 160. It is to be understood that a lateral slide would also be prepared and used in conjunction with an overlay 164 shown in FIG. 19 having an actual size lateral outline of the treatment volume drawn thereon. Once proper alignment is effected, the target center is thus determined in terms of true coordinates from the reference origin. In the example illustrated in FIG. 18, it may be appreciated that the lateral coordinate is zero and that the longitudinal coordinate is alightly over one centimeter in the negative direction (toward the feet of the patient).

THE PREFERRED METHOD — FIGS. 20–24

Figure 20:
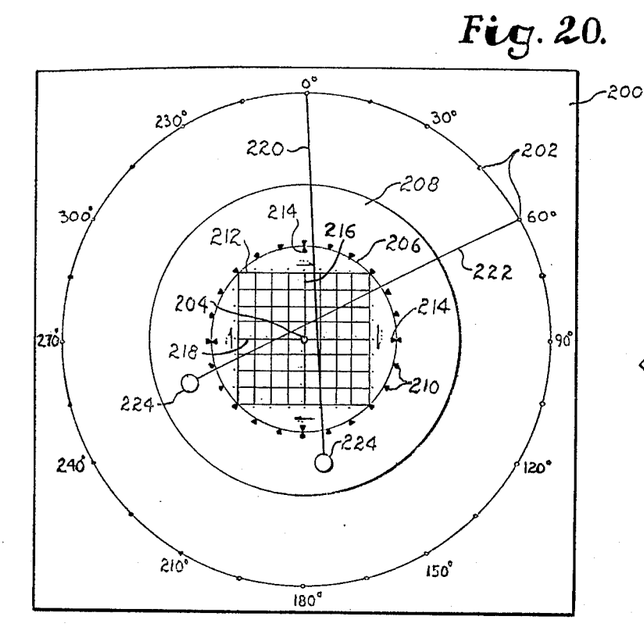
FIG. 20 is an elevational view of a two-dimensional simulation of the radiographic geometry, utilized in implementing the preferred localization method of the present invention.
Figures 21, 22, 23:
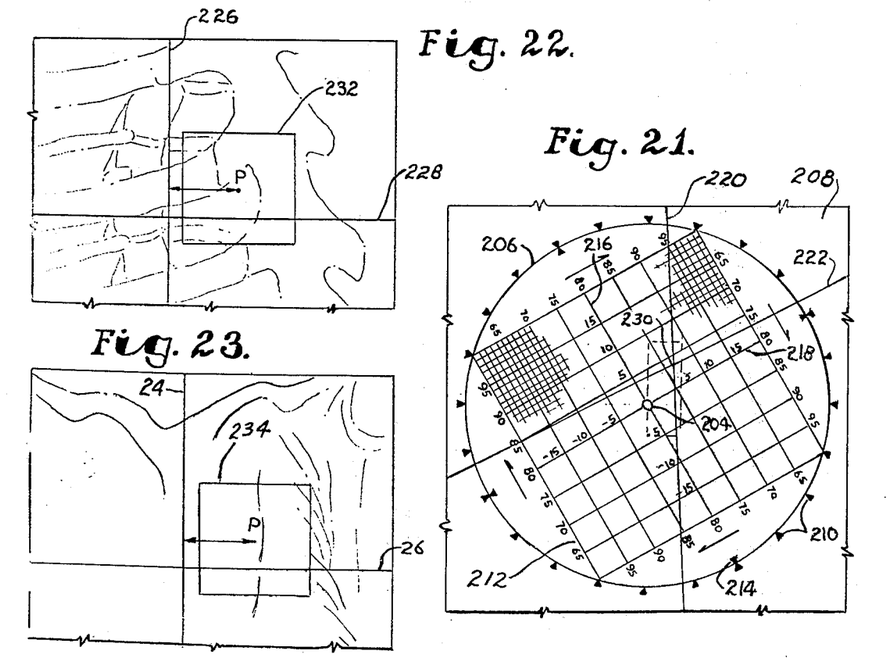
FIG. 21 is a fragmentary, enlarged view similar to FIG. 20, showing the rotatable grid in detail.
FIG. 22 is a fragmentary view of an exemplary radiograph obtained with the X-ray focus located at 60°.
FIG. 23 is a fragmentary view of an exemplary frontal radiograph (focus at 0°) showing the same tissue center as the radiograph of FIG. 22.

A two-dimensional simulation of the radiographic geometry is illustrated in FIGS. 20 and 21 and is utilized in conjunction with the teletherapy simulator 80 illustrated in FIG. 10 and discussed hereinabove. The simulation enables the true coordinates of the target center to be determined irrespective of the angular location of each of the X-ray focuses. Accordingly, this provides significantly increased versatility since biplane radiographs other than the usual anterior-posterior and lateral radiographs may be taken in localizing the target center for radiotherapy.

Referring to FIG. 20, a square backboard 200 simulates the plane of the X and Y axes illustrated in FIG. 1. A number of pegs 202 project outwardly from the backboard 200 toward the viewer, and are arranged in a circular pattern. The pegs 202 represent points that are possible locations of the focus of a radiograph. For convenience, every other point is identified by the angular location it represents, such as 0°, 30°, 60°, etc. Accordingly, correlating FIG. 20 with FIG. 1, the frontal focus 16 is at the 0° point on the backboard 200, and the lateral focus 14 is at the 90° point. The center 204 of the circular pattern represents the Z-axis illustrated in FIG. 1, and it may be imagined that the head of the patient is behind the backboard 200 and that he is lying generally along the Z-axis with his feet in front of the backboard 200. An imaginary line from any of the pegs 202 through the center 204 represents the central axis of the X-ray beam emanating from a focus at that location.

A disc 206 is mounted on the backboard 200 for free rotation about the center 204 representing the Z-axis. A flat, stationary ring 208 surrounds the rotatable disc 206 and is composed of a magnetic material. A number of marks 210 at the inside edge of the ring 208 are radially aligned with the various angular locations 202 occurring every 15° around the circular pattern.

The surface of the disc 206 is provided with intersecting lines forming a grid 212 that is, in effect, a centimeter scale. The lines of the grid seen in FIG. 20 are 5 cm apart; the enlarged view in FIG. 21 shows the individual centimeter lines. Index marks 214 appear at 90° intervals on the periphery of the disc 206 and are aligned with a pair of graduated axes 216 and 218, the graduations of which are formed by the intersecting centimeter lines.

As discussed previously with respect to FIGS. 10–19, the distance from the X-ray focus to the center of rotation 104 in the simulator 80 is known and is assumed, in this instance, to be 80 cm. Accordingly, the various focus locations 202 are radially spaced from the center 204 a distance of 80 cm to correspond to the geometry of the simulator 80. It will be recalled that the horizontal axis of rotation 84 illustrated in FIG. 10 is analogous to the Z-axis illustrated in FIG. 1. In FIGS. 20 and 21 it is assumed for purposes of illustration that the focus locations are 0° and 60° for the biplane radiographs obtained from operation of the simulator 80. As will be explained further hereinafter, a string 220 extending from the 0° peg 202 and a string 222 extending from the 60° peg 202 represent the rays from the two focuses passing through the target center. Small rings (not shown) on the ends of the strings 220 and 222 may conveniently be slipped over the pegs 202 to secure the ends of the strings to the desired pegs, the opposite ends of the strings being held in place by permanent magnets 224 which adhere by magnetic attraction to the ring 208.

In utilizing the geometric simulation illustrated in FIGS. 20 and 21 and described above, it will be further assumed for purposes of illustration that the two radiographs shown in FIGS. 22 and 23 are those that have been obtained at the 0° and 60° focuses. The radiograph obtained at the 0° focus is the usual frontal radiograph and is illustrated in FIG. 23, it being noted that this radiograph is much the same as that shown in FIG. 3 except that, in the present example, a different target center is designated. The radiograph obtained with the focus at 60° is shown in FIG. 22 and is similar to the lateral radiograph shown in FIG. 2, except that now the angle of the X-ray head has been raised 30° in order to properly show a target center that would be obscured by the rib cage if the focus were at 90°. Accordingly, it is evident at this juncture that the advantage of the geometric simulation lies in its ability to determine true coordinates in cases where the target center cannot be seen on either an anterior-posterior radiograph or a lateral radiograph, or both.

The target center is represented by the point P in the radiographs shown in FIGS. 22 and 23. As in the previously described localization techniques, the projection of the Z-axis is seen at 24 in the frontal radiograph of FIG. 23, and the projection of the X-axis is seen at 26. The cross wires of the teletherapy simulator 80 also cast an image of the Z-axis onto the radiograph of FIG. 22, as is seen at 226. Since the focus is at 60°, the projection 228 of the transverse axis does not represent either the X or the Y axis. However, the transverse axis and its projection 228 do lie in the same plane as the X and Y axes, and it is this plane, of course, that is simulated by the backboard 200. Accordingly, for purposes of subsequent discussion, the X-Y plane will be referred to as the reference plane, and the Z-axis will be considered to be the primary reference axis of the geometry.

The grid 212 is shown in detail in FIG. 21, where it may be noted that the disc 206 (and hence the grid 212 thereon) has been rotated 30° with respect to the illustration thereof in FIG. 20. Numerical indicia appear along the sides of the grid 212 and represent the focus-to-target center distances in centimeters. The number "80" appears at each end of the graduated axes 216 and 218 to designate the 80 centimeter distance from the various focus locations 202 to the center 204 at which the axes 216 and 218 intersect. It will be recalled that the center 204 simulates the Z-axis or primary reference axis and thus also represents the origin of the coordinate system. The other centimeter distances increase in the direction of the arrows appearing at the four sides of the grid 212, the full range of the centimeter scale in each direction being from 60 to 100 centimeters. Furthermore, the graduated axes 216 and 218 themselves are scaled from the origin 204 to 20 cm in plus and minus directions as is apparent from FIG. 21.

To aid in an understanding of the operation of the geometric simulation, FIG. 21 also includes a phantom illustration of a portion of the grid 212 of particular interest adjacent the center 204, such illustration showing the position of the grid lines with the disc 206 returned to the position thereof shown in FIG. 20. This zone of the grid is of particular interest inasmuch as the crossing point 230 of the strings 220 and 222 is contained therein.

The initial procedure followed in utilizing the localization apparatus of FIGS. 20 and 21 is the same as that as discussed hereinabove with respect to the direct reading localization method and apparatus of FIGS. 10–19. The patient is placed on the couch 86 of the simulator 80 of FIG. 10 in the treatment position, and the couch top and patient are then moved longitudinally, vertically and laterally until the target center is near the center of rotation 104, which corresponds to the origin represented by the center point 204 in the geometric simulation of FIGS. 20 and 21. The X-ray head 96 is provided with a light localizer to facilitate the marking of one upper and two lateral points on the patient, or treatment shell, to designate the position of the center of rotation 104. As discussed previously, the upper point is marked with the head directly overhead (0° location), and the lateral points are marked with the head rotated to the 90° and 270° locations. The alternative one-point localization procedure may also be used if desired.

After the radiographs are taken illustrated in FIGS. 22 and 23, they are appropriately marked to designate the projections of the target center and the treatment volume. In the 60° radiograph the target center P is within a treatment volume designated by the square 232; in the 0° radiograph the target center P is within the treatment volume designated by the square 234. The transverse coordinates of the target center P on the two radiographs are then measured, these distances being represented by the arrows. Such measurement is accomplished in a special manner as will now be discussed.

Figure 24:
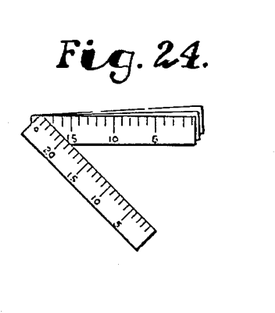
FIG. 24 is a view illustrating a set of magnified rulers utilized in practicing the preferred localization method.

FIG. 24 illustrates a set of magnified rulers used to measure distances on the radiographs. The rulers are centimeter scales that have been magnified to compensate for the inherent enlargement of distances in the radiographs caused by divergence of the X-rays as fully discussed hereinabove. Each of the rulers of the set represents a different distance from the X-ray focus to the object of interest. For complete coverage of all focus-to-object distances corresponding to the distances represented by the grid 212, an individual ruler would be provided for each centimeter increment from 60 to 100.

The magnified rulers are readily made by simply using a transparent centimeter ruler as the object and taking a radiograph with the object ruler at a known focus-to-object distance. The radiograph thus obtained shows the magnified scale for that focus-to-object distance. This procedure would be repeated as many times as necessary in order to obtain the magnified scales for all focus-to-object distances.

It will be assumed for purposes of illustration that the transverse coordinate in each of the radiographs of FIGS. 22 and 23 is 4 centimeters. As the arrows indicate, the transverse coordinate in the radiograph of FIG. 22 is measured from the projection 226 of the Z-axis to the target center P, whereas in the radiograph of FIG. 23 the transverse coordinate is measured from the projection 24 of the Z-axis to the target center P. Both of the transverse coordinate distances are in the positive direction as previously defined.

Referring now to FIG. 20, the disc 206 is shown in the proper position for plotting the transverse coordinate of the target center in the radiograph of FIG. 23 obtained from a focus located at 0°. The 4 cm distance has been measured on the radiograph using the magnified ruler corresponding to a focus-to-object distance of 80 cm. It is important to note that this is an assumed distance selected for convenience since it permits plotting directly on the axis 216 and 218, each of which corresponds to the 80 cm distance. It will be appreciated as this discussion proceeds that a different focus-to-object distance could be assumed, as long as plotting was then done on the corresponding line of the grid 212.

It may be seen in FIG. 20 that the string 220 is being held by the magnet 224 in crossing relationship to the axis 218 at the 4 cm graduation in the positive direction. The technician or physician using the simulation is, of course, aware of the focus location of a particular radiograph; accordingly, in this case the disc 206 is placed at the position illustrated in FIG. 20 where the positive side of one of the graduated axes 216 or 218 is to the right viewing FIG. 20, and where such axis is parallel to the radiographic plane.

The next step is to plot the transverse coordinate distance measured from the 60° radiograph of FIG. 22, which is also assumed to be 4 cm as measured with the magnified ruler corresponding to a focus-to-object distance of 80 cm. This is illustrated in FIG. 21 where it may be seen that the disc 206 has been rotated 30° counterclockwise so that the axis 216 is now parallel with the radiographic plane of the radiograph obtained at the 60° focus location. It may be observed that the string 222 crosses the axis 216 four centimeters from the center of origin 204 in the positive direction. Accordingly, the crossing point 230 is now defined by the strings 220 and 222 and represents the actual location of the target center in the geometric simulation.

Having located the actual position of the target center, the disc 206 is rotated back to the position thereof shown in FIG. 20 so that the true vertical (Y) and lateral (X) coordinates may be determined from the centimeter lines on the grid 212. Referring to the phantom illustration of the grid in FIG. 21, it may be seen that the vertical coordinate is approximately 6.5, and that the lateral coordinate is approximately 3.5. Thus, the technician has now determined the coordinates of the target center in the X-Y or reference plane. Furthermore, the grid 212 indicates the true focus-to-target center distances in the respective radiographs. Such distance is approximately 74 cm in the 60° radiograph of FIG. 22 as is clear in FIG. 21, where it may be seen that the crossing point 230 is closet to the 74 cm grid line parallel to the radiographic plane. By returning the disc 206 to the position thereof illustrated in FIG. 20, it is seen that the crossing point 230 is closest to the 73 cm grid line.

Regarding the reading of the grid 212 to determine the actual focus-to-target center distances to the nearest centimeter, it should be understood that the sense of the arrows at the sides of the grid 212 must be considered. Each of the arrows represents the general direction of the X-ray beam, thus the distances increase in the direction of each arrow. Accordingly, in determining the actual focus-to-target center distance in FIG. 21 for the 60° radiograph, the centimeter scale is read along the bottom so that the grid line closest to the crossing point 230 is read as "74" rather than "86".

Since the actual focus-to-target center distances are now known, the appropriate magnified ruler may be used in each radiograph to measure the longitudinal (Z) coordinate of the target center as well as the true length, width, and breadth of the treatment volume. With knowledge of the true coordinates of the target center, the patient is again placed on the simulator couch 86 and positioned with the center of rotation 104 at the reference origin previously marked when obtaining the radiographs. As discussed previously, the patient is then moved laterally, longitudinally and vertically through distances equal to the coordinates to thereby place the center of rotation 104 at the target center. The patient is now remarked using the light localizer within the X-ray head 96 so that the patient may subsequently be placed on the rotation radiotherapy machine and properly positioned without the necessity of shifting the patient through the coordinates.

Having thus described the invention, what is claimed as new and desired to be secured by Letters Patent is:

1. Means for determining the coordinates of a target center with respect to first, second and third mutually orthogonal reference axes defining an origin, where projections of the target center and said first axis appear on each of a pair of biplane radiographs from which a transverse coordinate may be measured, each radiograph having been obtained in a radiograph plane parallel to said first axis and the focus-to-origin distance being known, said means comprising:

means presenting a planar surface simulating the plane of said second and third axes, said surface being provided with points arranged in a circular pattern having a center representing said first axis, said points being radially spaced said distance from said center and representing possible angular locations of the focus for each radiograph;

a grid on said surface substantially in the plane thereof, disposed within said pattern, and including a pair of orthogonal, graduated axes intersecting said center to represent said origin, said grid being rotatable about said center to plotting positions aligning said graduated axes in parallel and perpendicular relationship respectively with the plane representing the radiographic plane of each radiograph, said grid having one angular position in which the graduated axes thereof simulate said second and third reference axes; and means for indicating the paths of rays from two of said points representing angularly spaced focus locations through the transverse coordinates of the target center plotted on said grid, whereby the grid indicates the coordinates of the target center with respect to said second and third reference axes when the grid is in said one position, and further indicates the focus-to-target center distances for the radiographs when the grid is in said plotting positions.

2. The determining means as claimed in claim 1, wherein said indicating means presents a pair of stationary lines overlying said grid.

3. The determining means as claimed in claim 1, wherein is provided a ring of magnetic material on said surface surrounding said grid, said indicating means including a pair of strings extending from said two focus locations and having magnets attached thereto to hold the strings in fixed positions across said grid by attraction of the magnets to said ring.

* * * * *